United States Patent [19]

Deshmukh et al.

[11] Patent Number: 4,967,007
[45] Date of Patent: Oct. 30, 1990

[54] IMPROVED PROCESS FOR THE PREPARATION OF 1-SUBSTITUTED AMINO-1-SUBSTITUTED THIO-2-NITRO ALKENES

[75] Inventors: Abdul R. A. S. Deshmukh; Baburao M. Bhawal; Vasudeo P. Shiralkar; Srinivasachari Rajappa, all of Maharashtra, India

[73] Assignee: Council of Scientific & Industrial Research, New Delhi, India

[21] Appl. No.: 353,388

[22] Filed: May 16, 1989

[51] Int. Cl.$^5$ .................. C07C 321/00; C07C 323/00; C07C 381/00

[52] U.S. Cl. ...................................... 564/501; 558/2; 562/28

[58] Field of Search .................... 564/501, 500; 558/2; 562/28

[56] References Cited

U.S. PATENT DOCUMENTS 3,322,788 5/1967 Gompper et al. ...................... 558/2
4,025,529 5/1977 Kollmeyer ........................... 564/501

FOREIGN PATENT DOCUMENTS 060049 9/1982 European Pat. Off. ............... 558/2

OTHER PUBLICATIONS

Evers et al. Z. Chem., vol. 20, pp. 413–414 (1980).
Schulze et al., Z. Chem., vol. 20, pp. 207–209 (1980).
Garin et al., Synthesis, 1983, pp. 375–376.
Corey et al., Tetrahedron Letters, No. 39, pp. 3817–3820 (1973).
Metzger et al., Chem. Ber., vol. 101, pp. 1131–1133 (1968).
Ainley et al., J. Chem. Soc., vol. 65, pp. 147–152 (1944).
McIntosh, "Phase-Transfer Catalysis Using Quaternary 'Onium Salts," Journal of Chemical Education, vol. 55, No. 4, (1978), pp. 235–238.

Primary Examiner—Glennon H. Hollrah
Assistant Examiner—Scott C. Rand
Attorney, Agent, or Firm—Abelman Frayne Reza & Schwab

[57] ABSTRACT

A process is disclosed for the manufacture of 1-substituted amino-1-substituted thio-2 nitro alkenes of the general formula: (R1NH) (R2S) C=CR3 (NO2) wherein R1, R2, R3, may be same or different and may consist of hydrogen, alkyl, aryl or arylalkyl groups or combinations thereof. These alkenes are prepared by reacting a primary amine with a compound of sulfur in the presence of a primary catalyst to obtain a carbonimidodithioic acid salt which is converted to a corresponding ester which is thereafter reacted with a nitro compound in the presence of a secondary catalyst. 1-methylamino-1-methylthio-2-nitroethene is an important intermediate in the synthesis of Rantitidine and Nizatidine which are used as effective drugs in the treatment of peptic ulcers and associated gastrointestinal disorders.

13 Claims, No Drawings

IMPROVED PROCESS FOR THE PREPARATION OF 1-SUBSTITUTED AMINO-1-SUBSTITUTED THIO-2-NITRO ALKENES

This invention relates to a process for the preparation of nitrovinyl derivatives. More particularly, it relates to the preparation of 1-substituted amino-1-substituted thio-2-nitro alkenes of the general formula (I)

$(R_1NH)(R_2S)C=CR_3(NO_2)$   I wherein $R_1$, $R_2$, $R_3$ may be same or different and may consist of hydrogen, alkyl, aryl, arylalkyl groups or combinations thereof.

More specifically, the present invention relates to the preparation of 1-methylamino-1-methylthio-2-nitroethene (II), an important intermediate in the synthesis of antiulcer drugs such as ranitidine (V) and nizatidine (VI).

$R(CH_3S)C = CHNO_2$

II  R = $-NHCH_3$
III R = $-S(O)CH_3$
IV R = $-SCH_3$ $(CH_3)_2NCH_2 \underset{O}{\overset{\phantom{x}}{\diagup\diagdown}} CH_2SR$ V R = $-CH_2CH_2NH-\underset{NHCH_3}{\overset{C=CHNO_2}{|}}$

VII R = $-CH_2CH_2NH_2$
VIII R = H $(CH_3)_2NCH_2 \underset{S}{\overset{N}{\diagup\diagdown}} CH_2SCH_2CH_2NH-\underset{NHCH_3}{\overset{C=CHNO_2}{|}}$   VI

BACKGROUND OF THE INVENTION

Ranitidine (V) and nizatidine (VI) are extremely potent histamine $H_2$-receptor antagonists. They are used as effective drugs in peptic ulcers and associated gastrointestinal disorders.

The synthesis of Ranitidine (V) involves condensation of 1-methylamino-1-methylthio-2-nitroethene (II) and 2-(((5-(dimethylamino) methyl-2-furanyl)methyl)thio) ethanamine (VII) (Spanish Patent ES No. 501,844 (1982); Spanish Patent ES No. 502,940 (1982). In another approach for ranitidine (V), 1-methylamino-1-methylthio-2-nitroethene (II) is reacted with ethylenimine and the product so obtained is condensed with ((5-(dimethylamino)methyl-2-furanyl)-methyl mercaptan (VIII) (Belgium Patent Application BE No. 888,747 (1981); Spanish Patent ES No. 529,532 (1986).

In the prior art, the preparation of 1-methylamino-1-methylthio-2-nitroethene (II) involves amination of sulfoxide III. German Offen No. 2,621,092 (1976), for example, describes the preparation of II by the reaction of methylamine with sulfoxide III. European Patent EP No. 58,492 (1982) and Belgium Patent Application BE No. 888,747 (1981) describe the preparation of 1-methylamino-1-methylthio-2-nitroethene (II) by amination of 1,1-bismethylthio-2-nitroethene (IV) with methylamine.

In all the above processes, constituting the prior art, methylamine is reacted with the substrates (III) or (IV). In this reaction, the high nucleophilicity of methylamine results in the rapid reaction of the required product (II) with a second molecule of methylamine. This unwanted reaction results in the formation of the by-product 1,1-bismethylamino-2-nitroethene (IX).

$(CH_3NH)_2C=CHNO_2$   IX

The removal of this from the required product (II) poses problems in purification and consequently the yield is reduced. In the prior art process, this problem is sought to be overcome by stopping the reaction at below 50% conversion. This involves recovery and recycling of starting material thereby increasing the number of operations.

SUMMARY OF THE INVENTION

The present invention provides for an improved process for the preparation of 1-substituted amino-1-substituted thio-2-nitroethenes of the general formula I wherein the drawbacks of prior art processes mentioned hereinabove are minimized. This improved process involves reaction of a primary amine with a sulfur compound selected from the group consisting of carbon disulfide and dialkyltrithiocarbonate in the presence of a primary catalyst to obtain a carbonimidodithioic acid salt, and converting this salt to the corresponding carbonimidodithioic acid ester. This ester is further reacted with a nitro compound in the presence of a secondary catalyst to obtain the above mentioned compound of the general formula I.

Thus, in one embodiment of the present invention, carbonimidodithioic acid ester of formula X $(R_1-N=C(SR_2)(SR_3)$ wherein $R_1$, $R_2$, $R_3$ are methyl ($CH_3$), is reacted with nitromethane in the presence of a catalyst at a temperature ranging from room temperature to 150° C. In a preferred embodiment of the present invention, the reaction may be carried out in the presence of suitable solvents such as benzene, toluene, xylene, chlorobenzene, dimethyl formamide, or chloro hydrocarbons (e.g. dichloromethane). As catalysts, Lewis acids such as boron trifluoride, solid catalysts such as zeolites exemplified by ZSM-5, H-ZSM-5, X and Y type, and zeolites containing rare earth and alkali metal ions may be used, such as faujasite and mordenite.

The carbonimidodithioic acid dimethyl ester of formula (X) may be prepared by reacting a primary amine with carbon disulfide in an organic solvent (e.g. benzene) in the presence of an aqueous base (e.g. sodium hydroxide) using phase transfer catalyst (e.g. triethylbenzyl ammonium bromide) tetrabutylammonium bromide or tris (2-methoxyethoxy). ethylamine (TDA-1) as the primary catalyst. The alkylation of carbonimidodithioic acid salt with alkyl halide or dialkyl sulfate (dimethyl sulfate) at 0° to room temperature gives substituted carbonimidodithioic acid ester (X).

One of the characteristics of the present invention is the direct conversion of carbonimidodithioic acid ester into 1-substituted amino-1-substituted thio-2-nitroethene in a single step.

Another characteristic of the present invention is the use of solid catalysts, preferably zeolites in the conversion of carbonimidodithioic acid ester into 1-substituted amino-1-substituted thio-2-nitroethene.

One of the basic advantages of the present invention over prior art process for the preparation of II and related compounds is that the formation of 1,1-bismethylamino-2-nitroethene (IX) is totally eliminated, thereby increasing the yield of the required product II. The solid catalyst can be recovered by filtration and reused. The ease of operation is a significant advantage of the process according to the present invention.

The improved process of this invention will now be described with a few examples which are for illustrative purposes only and are not to be construed as limitations on the scope of the invention.

EXAMPLE 1

Methyl carbonimidodithioic acid dimethyl ester (X)

To a cooled mixture of sodium hydroxide (42 g), water (45 ml), benzene (45 ml) and tetrabutyl ammonium bromide (1.3 g), methylamine hydrochloride (13.4 g) was added slowly. Carbon disulfide (12 ml) was added to this mixture at 10°–15° C. with stirring. It was then stirred for 15 minutes and dimethyl sulfate (72 ml) was added dropwise at 10°–15° C. in 1 hr. The mixture was stirred at room temperature for 3 hr. The benzene layer was removed and the aqueous layer was extracted with benzene. Removal of solvent gave the required title compound (X, 23 g) as a pale yellow oil. b.p. 187°–190° C.

IR (neat): 1600, 1435, 1400, 1015, 910 $cm^{-1}$.

NMR ($CDCl_3$): 2.26 (s, 3H), 2.5 (s, 3H), 3.20 (s, 3H).

EXAMPLE 2

Benzyl carbonimidodithioic acid dimethyl ester (XI)
$R_1$—N═C ($SR_2$) ($SR_3$) wherein $R_1$=Benzyl,
$R_2=R_3=CH_3$ To a cooled mixture of sodium hydroxide (6 g), water (10 ml) benzene (30 ml), tetrabutyl ammonium bromide (0.5 g) and benzylamine (5.35 g), carbon disulfide (6 ml) was added with stirring. Methyl iodide (8 ml) was added slowly at 10°–15° C. The mixture was stirred at room temperature for 3 hr. The benzene layer was removed and the aqueous layer was extracted with benzene. Removal of benzene gave 9.1 g of the title compound XI.

b.p. 100°–110° C./8 mm.

IR (neat): 1595, 1580, 1020, 920, 730 cm.

NMR ($CCl_4$): 2.40 (s, 3H), 2.53 (s, 3H), 4.33 (s, 2H), 7.26 (m, 5H).

EXAMPLE 3

1-Methylamino-1-methylathio-2-nitroethene II

A mixture of nitromethane (3 ml), methyl carbonimidodithioic acid dimethyl ester (X, 675 mg), rare earth exchange Y-zeolite (RE 70 Na Y) (675 mg) was heated at 90°–110° C. for 72 hr. It was filtered and the solvent was removed by distillation leaving the required 1-methylamino-1-methylthio-2-nitroethene (II) as residue. m.p. 112°–114° C.

IR (nujol): 3200, 1570, 1450, 1370, 1240, 4950 cm.

NMR (CDCl): 2.40 (s, 3H), 3.12 (d, 3H), 6.55 (s, 1H), 10.25 (brs, 1H).

EXAMPLE 4

1-Methylamino-1-methylthio-2-nitroethene II

A mixture of nitromethane (3 ml), compound X (600 mg), and zeolite (ZSM-5) (600 mg) was refluxed for 87 hr. The solid catalyst was filtered off and the filtrate on concentration under reduced pressure gave the required product II, characterized by m.m.p. and spectral data as given in example 3.

EXAMPLE 5

1-Methylamino-1-methylthio-2-nitroethene II

Nitromethane (5 ml) was added to a mixture of compound X (900 mg) and zeolite, HZSM-5 (900 mg) and heated to reflux for 72 hr. The catalyst was removed by filtration and the required product II was isolated and characterized as described in example 3.

EXAMPLE 6

1-Methylamino-1-methylthio-2-nitroethene II

A mixture of nitromethane (3 ml), compound X (560 mg), and zeolite, RE 50 Na X (560 mg) was refluxed for 72 hr. The catalyst was removed by filtration and product II was isolated and characterized as in example 3.

EXAMPLE 7

1-Methylamino-1-methylthio-2-nitroethene II

A mixture of compound X (675 mg), nitromethane (400 mg), zeolite, RE 70 Na Y (675 mg) and benzene (5 ml) was refluxed for 72 hr. The reaction mixture was filtered and the filtrate concentrated to give the product II and characterized as in example 3.

EXAMPLE 8

1-Methylamino-1-methylthio-2-nitroethene II

A mixture of nitromethane (5 ml), compound X (800 mg) and zeolite, H Y type, (800 mg) was refluxed for 80 hr. The product II was isolated and characterized as in example 3.

EXAMPLE 9

1-Methylamino-1-methylthio-2-nitroethene II

A mixture of compound X (840 mg), nitromethane (6 ml) and zeolite, RE 80 Na X, (800 mg) was heated at 90° to 110° C. for 48 hr. It was filtered and nitromethane was recovered by distillation. The residue was treated with pet. ether and the solid isolated by filtration and characterized as compound II as in example 3.

EXAMPLE 10

1-Methylamino-1-methylthio-2-nitroethene II

A mixture of nitromethane (5 ml), zeolite, RE 70 Na-Y (5 g) and compound X (5 g) in toluene (20 ml) was refluxed for 48 hr. The catalyst was filtered off and the filtrate was concentrated to give the product II which was characterized as in example 3.

EXAMPLE 11

1-Benzylamino-1-methylthio-2-nitroethene XII

A mixture of nitromethane (4 ml), zeolite, RE 70 Na-Y (500 mg) and benzyl carbonimidodithioic acid dimethyl ester (XI, 500 mg) was refluxed for 110 hr. It was filtered and filtrate concentrated and treated with pet. ether. The solid that separated out was filtered and characterized as compound XII.

m.p. 158–161.

IR: 1560, 1270, 1235, 950, 730 cm.

NMR ($CDCl_3$): 2.40 (s, 3H), 4.55 (d, J=8 hz, 2H) 6.50 (s, 1H), 7.25 (s, 5H), 10.60 (brs, 1H).

EXAMPLE 12

1-Methylamino-1-methylthio-2-nitroethene II

A mixture of nitromethane (400 mg), compound X (675 mg), BF etherate (50 mg), dichloromethane (3 ml) was refluxed overnight in the presence of a catalyst containing a rare earth exchanged faujasite. The product formation was monitored by thin layer chromatography. The required product II was isolated and characterized as in example 3.

We claim:

1. An improved process for the preparation of 1-substituted amino-1-substituted thio-2-nitro alkenes of general formula $(R_1NH)(R_2S)C=CR_3(NO_2)$ wherein $R_1$, $R_2$, $R_3$, may be same or different and may consist of hydrogen, alkyl, aryl or arylalkyl groups or combinations thereof, which comprises reacting a primary amine with a compound of sulfur selected from the group consisting of carbon disulfide and dialkyltrithiocarbonate in the presence of a primary catalyst to obtain a carbonimidodithioic acid salt, converting the said salt to the corresponding carbonimidodithioic acid ester and reacting said ester with a nitro methane in the presence of a zeolite as a secondary catalyst to obtain the 1-substituted amino-1-substituted thio-2-nitro alkenes.

2. A process according to claim 1 wherein $R_1$ is an alkyl group with more than one carbon atom, aryl or arylalkyl group.

3. A process according to claim 1 wherein $R_1$ is methyl.

4. A process according to claim 1 wherein $R_2$ is alkyl, aryl or arylalkyl.

5. A process according to claim 1 wherein $R_2$ is methyl.

6. A process according to claim 1 wherein $R_3$ is H.

7. A process according to claim 1 wherein $R_3$ is alkyl, aryl or arylalkyl.

8. A process according to claim 1 wherein the primary amine is methylamine.

9. A process according to claim 1 wherein the primary catalyst is a phase transfer catalyst.

10. A process according to claim 9 wherein the phase transfer catalyst is benzyltriethylammonium bromide or tetrabutylammonium bromide or tris (2-methoxyethoxy)ethylamine (TDA-1).

11. A process according to claim 1 wherein the zeolite secondary catalyst is selected from a rare earth exchanged faujasite, mordenite, and a ZSM-5 zeolite.

12. A process according to claim 1 wherein the carbonimidodithioic acid ester is methylcarbonimidodithioic acid dimethyl ester.

13. A process according to claim 1 wherein methylcarbonimidodithioic acid dimethyl ester is reacted with nitromethane in the presence of a secondary catalyst containing a rare earth exchanged faujasite to form 1-methylamino-1-methylthio-2-nitroethene.

* * * * *